(12) United States Patent
Kothandaraman

(10) Patent No.: US 9,186,518 B2
(45) Date of Patent: Nov. 17, 2015

(54) MEDICAL DEVICE APPLICATION FOR CONFIGURING A MOBILE DEVICE INTO AN EXTERNAL CONTROLLER FOR AN IMPLANTABLE MEDICAL DEVICE

(71) Applicant: Boston Scientific Neuromodulation Corporation, Valencia, CA (US)

(72) Inventor: Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/470,221

(22) Filed: Aug. 27, 2014

(65) Prior Publication Data

US 2015/0073498 A1 Mar. 12, 2015

Related U.S. Application Data

(60) Provisional application No. 61/874,863, filed on Sep. 6, 2013.

(51) Int. Cl.
*A61N 1/372* (2006.01)
*G06F 9/44* (2006.01)
(Continued)

(52) U.S. Cl.
CPC .......... *A61N 1/37264* (2013.01); *A61N 1/3605* (2013.01); *A61N 1/37235* (2013.01); *G06F 9/441* (2013.01); *G06F 9/4401* (2013.01);
(Continued)

(58) Field of Classification Search
CPC .......... A61N 1/3605; A61N 1/37264
USPC .......... 607/59
See application file for complete search history.

(56) References Cited

U.S. PATENT DOCUMENTS

| 5,548,271 A | 8/1996 | Tsuchiyama et al. |
| 5,720,770 A | 2/1998 | Nappholz et al. |

(Continued)

FOREIGN PATENT DOCUMENTS

WO 2003/095024 11/2003

OTHER PUBLICATIONS

International Search Report and Written Opinion regarding corresponding PCT Application No. PCT/US2014/053166, dated Oct. 23, 2014.

(Continued)

*Primary Examiner* — Carl H Layno
*Assistant Examiner* — Jennifer Ghand
(74) *Attorney, Agent, or Firm* — Lewis & Reese, PLLC

(57) ABSTRACT

A Medical Device Application (MDA) operates on the mobile device to temporarily configure it into a known secure configuration for use as an external controller, and to prevent operation of the mobile device inconsistent with this function. In particular, the MDA operates to (1) disable or reconfigure hardware modules, and/or (2) terminate or suspend software tasks, that might corrupt operation of the mobile device as an external controller. The MDA can comprise an application ("app") that the patient can download onto his mobile device and run to initialize the mobile device into the known secure configuration. The MDA also preferably provides a graphical user interface to allow a user to communicate with the implantable medical device using the now-secure mobile device. After using the mobile device to communicate with the implantable medical device, the MDA can be exited and the mobile device returned to its original configuration.

10 Claims, 14 Drawing Sheets

(51) Int. Cl.
 *A61N 1/36* (2006.01)
 *G06F 19/00* (2011.01)
 *G06Q 50/22* (2012.01)

(52) U.S. Cl.
 CPC .......... *G06F9/4411* (2013.01); *G06F 19/3406* (2013.01); *G06Q 50/22* (2013.01); *A61N 1/37247* (2013.01)

(56) References Cited

U.S. PATENT DOCUMENTS

| | | | |
|---|---|---|---|
| 5,759,199 | A | 6/1998 | Snell et al. |
| 6,219,580 | B1 | 4/2001 | Faltys et al. |
| 6,250,309 | B1 | 6/2001 | Krichen et al. |
| 6,434,429 | B1 | 8/2002 | Kraus et al. |
| 6,442,432 | B2 | 8/2002 | Lee |
| 6,490,487 | B1 | 12/2002 | Kraus et al. |
| 6,497,655 | B1 | 12/2002 | Linberg et al. |
| 6,516,227 | B1 | 2/2003 | Meadows et al. |
| 6,553,262 | B1 | 4/2003 | Lang et al. |
| 6,574,509 | B1 | 6/2003 | Kraus et al. |
| 6,662,052 | B1 | 12/2003 | Sarwal et al. |
| 6,738,671 | B2 | 5/2004 | Christophersom et al. |
| 7,043,305 | B2 | 5/2006 | KenKnight et al. |
| 7,060,030 | B2 | 6/2006 | Von Arx et al. |
| 7,191,012 | B2 | 3/2007 | Boveja et al. |
| 7,313,529 | B2 | 12/2007 | Thompson |
| 7,369,897 | B2 | 5/2008 | Bojeva et al. |
| 7,475,245 | B1 | 1/2009 | Healy et al. |
| 7,742,821 | B1 | 6/2010 | Vamos et al. |
| 7,848,819 | B2 | 12/2010 | Goetz et al. |
| 7,865,242 | B2 | 1/2011 | Diebold et al. |
| 7,885,712 | B2 | 2/2011 | Goetz et al. |
| 7,978,062 | B2 | 7/2011 | LaLonde et al. |
| 8,002,700 | B2 | 8/2011 | Ferek-Petric et al. |
| 8,103,346 | B2 | 1/2012 | Mass et al. |
| 8,130,093 | B2 | 3/2012 | Mazar et al. |
| 8,140,160 | B2 | 3/2012 | Pless et al. |
| 8,174,395 | B2 | 5/2012 | Samuelsson et al. |
| 8,265,757 | B2 | 9/2012 | Mass et al. |
| 8,373,556 | B2 | 2/2013 | LaLonde et al. |
| 8,395,498 | B2 | 3/2013 | Gaskill et al. |
| 8,410,940 | B2 | 4/2013 | Samuelsson et al. |
| 8,588,925 | B2 | 11/2013 | Carbunaru et al. |
| 8,868,794 | B2 * | 10/2014 | Masoud et al. .................. 710/5 |
| 2004/0088374 | A1 | 5/2004 | Webb et al. |
| 2004/0138517 | A1 | 7/2004 | Osorio et al. |
| 2005/0107839 | A1 | 5/2005 | Sanders |
| 2005/0283198 | A1 | 12/2005 | Haubrich et al. |
| 2006/0212092 | A1 | 9/2006 | Pless et al. |
| 2007/0088406 | A1 | 4/2007 | Bennett et al. |
| 2008/0103546 | A1 | 5/2008 | Patel et al. |
| 2008/0140157 | A1 * | 6/2008 | Goetz et al. ..................... 607/59 |
| 2008/0208292 | A1 | 8/2008 | Persen et al. |
| 2009/0024179 | A1 | 1/2009 | Dronov |
| 2009/0063187 | A1 | 3/2009 | Johnson et al. |
| 2009/0112281 | A1 | 4/2009 | Walhstrand |
| 2009/0118796 | A1 | 5/2009 | Chen et al. |
| 2009/0172640 | A1 | 7/2009 | Geismar et al. |
| 2009/0210798 | A1 | 8/2009 | Wu et al. |
| 2009/0292340 | A1 | 11/2009 | Mass |
| 2010/0229324 | A1 | 9/2010 | Conrad |
| 2010/0292556 | A1 | 11/2010 | Golden |
| 2010/0305663 | A1 | 12/2010 | Aghassian |
| 2010/0318159 | A1 | 12/2010 | Aghassian et al. |
| 2011/0071597 | A1 | 3/2011 | Aghassian |
| 2011/0112611 | A1 | 5/2011 | Aghassian |
| 2012/0163663 | A1 | 6/2012 | Masoud et al. |
| 2012/0215285 | A1 | 8/2012 | Tahmasian et al. |
| 2012/0265266 | A1 | 10/2012 | Colborn |
| 2013/0007210 | A1 | 1/2013 | Mass et al. |
| 2013/0073005 | A1 | 3/2013 | Aghassian |
| 2013/0076535 | A1 | 3/2013 | Sievert et al. |
| 2013/0123881 | A1 | 5/2013 | Aghassian |
| 2013/0210365 | A1 * | 8/2013 | Karuppiah et al. .......... 455/63.1 |
| 2014/0304773 | A1 | 10/2014 | Woods et al. |
| 2014/0365654 | A1 | 12/2014 | Huerto et al. |

OTHER PUBLICATIONS

Kothandaraman, Sridhar, "Replaceable RF Communications Card for Implantable Medical Device Programmers", Prior Art Database Technical Disclosure, pp. 1-4 (Jul. 3, 2003).
U.S. Appl. No. 61/832,072, filed Jun. 6, 2013, Huerto et al.

* cited by examiner

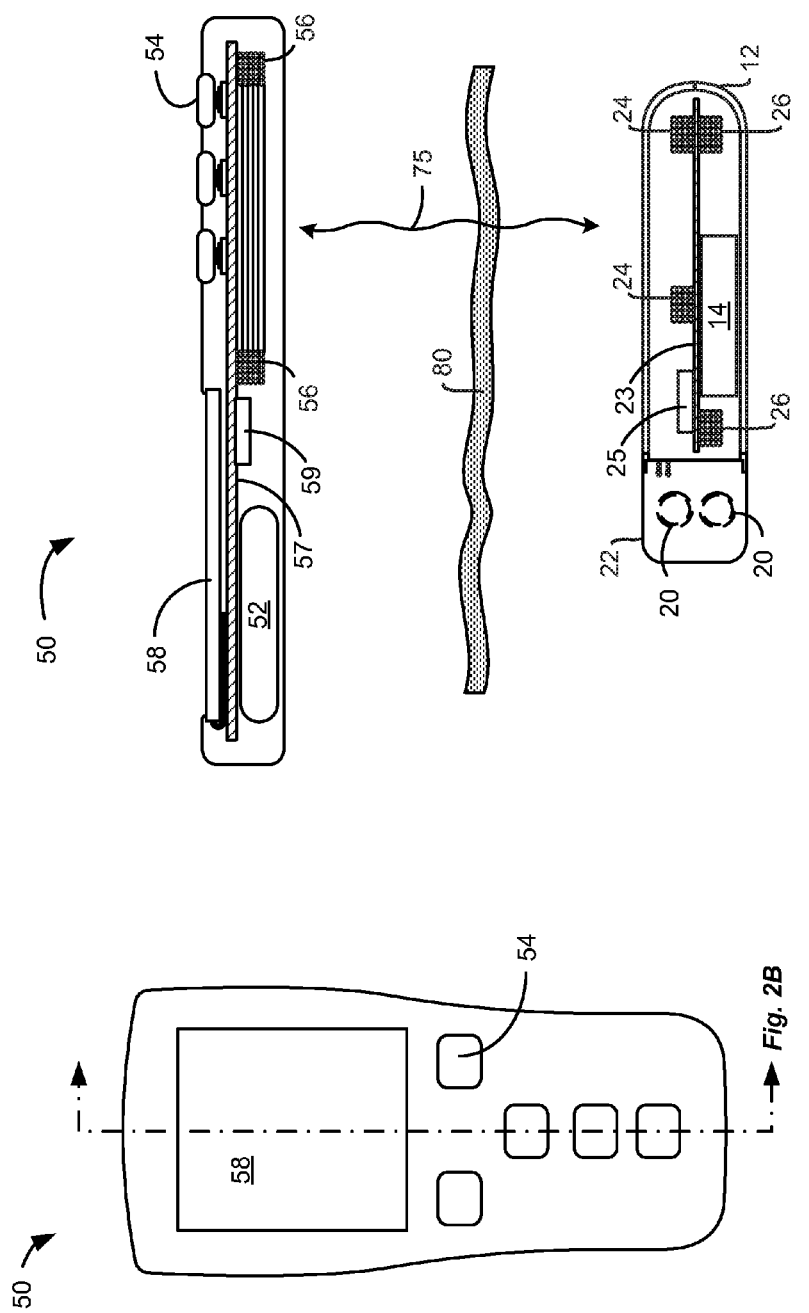

Figure 7A (213)

| Telephony | 11 MB |
| --- | --- |
| Music Player | 9.7 MB |
| E-mail | 7.8 MB |
| E-mail Synch | 2.2 MB |
| User Interface | 23 MB |
| Game 1 | 3.3 MB |
| MDA | 13 MB |
| Map | 3.7 MB |
| Task 4 | 21 MB |
| Task Manager | 0.6 MB |
| Clock | 0.7 MB |
| Task 1 | 3.4 MB |
| Push Service | 7.7 MB |
| Internet | 4.4 MB |

Figure 7B (214)

| Clock |
| --- |
| Antivirus |
| User Interface |
| MDA |
| Task Manager |
| Task 1 |
| Task 2 |

| E-mail Synch |
| --- |
| Software Updates |
| Alarm Clock |
| Telephony |
| E-mail |
| Task 3 |
| Task 4 |

| User Interface | 23 MB |
| --- | --- |
| MDA | 13 MB |
| Task Manager | 0.6 MB |
| Clock | 0.7 MB |
| Task 1 | 3.4 MB |

Figure 7E (226)

| Telephony | 11 MB |
| --- | --- |
| E-mail | 7.8 MB |
| E-mail Synch | 2.2 MB |
| Task 4 | 21 MB |

Figure 7F (224)

| Music Player |
| --- |
| Game 1 |
| Map |
| Push Service |
| Internet |

MEDICAL DEVICE APPLICATION FOR CONFIGURING A MOBILE DEVICE INTO AN EXTERNAL CONTROLLER FOR AN IMPLANTABLE MEDICAL DEVICE

CROSS-REFERENCE TO RELATED APPLICATIONS

This is a non-provisional of U.S. Provisional Patent Application Ser. No. 61/874,863, filed Sep. 6, 2013, which is incorporated herein by reference in its entirety, and to which priority is claimed.

This application is related to U.S. Provisional Patent Application Ser. No. 61/874,877, filed Sep. 6, 2013, entitled "Modified Booting Process for a Mobile Device to Configure It as an External Controller for an Implantable Medical Device."

FIELD OF THE INVENTION

The present invention relates generally to implantable medical device systems, and, more particularly, to mobile external devices to be used in implantable medical device systems.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

As shown in FIG. 1, a SCS system typically includes an Implantable Pulse Generator (IPG) 10, which includes a biocompatible device case 12 formed of titanium, for example. The case 12 typically holds the circuitry and battery 14 necessary for the IPG to function. The IPG 10 is coupled to electrodes 16 via one or more electrode leads 18 (two of which are shown). The electrodes 16 are coupled to the IPG 10 at one or more lead connectors 20 fixed in a header 22, which can comprise an epoxy for example. In the illustrated embodiment, there are sixteen electrodes, although the number of leads and electrodes is application specific and therefore can vary. In a SCS application, two electrode leads 18 are typically implanted on the right and left side of the dura within the patient's spinal cord. The proximal ends of the leads 18 are then tunneled through the patient's flesh to a distant location, such as the buttocks, where the IPG case 12 is implanted, at which point they are coupled to the lead connector(s) 20.

FIG. 2A shows a front view of an external controller 50 for communicating with the IPG 10, and FIG. 2B shows the external controller 50 and IPG 10 in cross section. Two coils (antennas) are generally present in the IPG 10: a telemetry coil 24 used to transmit/receive data via a wireless communications link 75 to/from the external controller 50; and a charging coil 26 for charging or recharging the IPG's battery 14 using an external charger (not shown). These and other components 25 necessary for IPG operation are electrically coupled to a circuit board 23. The telemetry coil 24 can be mounted within the header 22 of the IPG 10, or can be located within the case 12 as shown.

The external controller 50, such as a hand-held programmer or a clinician's programmer, is used to send or adjust the therapy settings the IPG 10 will provide to the patient (such as which electrodes 16 are active, whether such electrodes sink and source current, and the duration, frequency, and amplitude of pulses formed at the electrodes, etc.). The external controller 50 can also act as a receiver of data from the IPG 10, such as various data reporting on the IPG's status and the level of the IPG 10's battery 14. The external controller 50 is itself powered by a battery 52, but could also be powered by plugging it into a wall outlet for example. A user interface similar to that used for a cell phone is provided to operate the external controller 50, including buttons 54 and a display 58. The external controller 50 also includes a telemetry coil 56. These and other components 59 necessary for IPG operation are electrically coupled to a circuit board 57.

Wireless data transfer between the IPG 10 and the external controller 50 typically takes place via magnetic inductive coupling between coils 24 and 56, each of which can act as the transmitter or the receiver to enable two-way communication between the two devices. A Frequency Shift Keying (FSK) protocol can be used to send data between the two coils 24 and 56 via link 75. Although use of an FSK protocol in legacy systems is discussed below, use of this protocol is not universal, and other protocols employing different forms of modulation can be used to communicate between an external controller and an IPG, as one skilled in the art understands. Telemetry of data can occur transcutaneously though a patient's tissue 80.

Historically, external medical devices such as external controller 50 have been built by the manufacturer of the IPGs, and thus such external devices are generally dedicated to only communicate with such IPGs. The inventor has realized that there are many commercial mobile devices, such as mobile cell phones and multi-function tablets, that have the necessary configurable hardware and software to function as an external controller for an IPG or other implantable medical device. Using such mobile devices as external controllers for an implantable medical device would benefit both manufacturers and end users: manufacturers would not need to build dedicated external controllers that end users must buy, and end users could control their IPGs without the inconvenience of having to carry additional custom external controllers.

However, there are problems with this solution. Mobile devices are often configured with necessary hardware and software to communicate with other devices using short-range protocols, such as Bluetooth, Bluetooth Low Energy (BLE), Near Field Communication (NFC), Zigbee, and WiFi, as well as by using long-range cellular telephony protocols, any of which can be used to ultimately wireless connect the mobile device to the Internet or other network. While such communication channels allow for communication with an implantable medical device, they also render mobile devices less secure than traditional dedicated external controllers, particularly because they are prone to cyber attack, to computer viruses or malware, or to other intentional forms corruption. The multi-functional nature of mobile devices also makes them more prone to unintentional corruption, as their complicated nature may simply cause them to function improperly, even if they haven't been intentionally corrupted. Thus, if mobile devices are used as medical devices to communicate with implantable devices, there is an increased risk that the implantable medical device could be mis-programmed and potentially injure a patient.

Further, external medical devices are governed by FDA regulations such as 21 C.F.R. 820, which set forth requirements for class III medical devices such as external controllers. These rules require levels of safety and security that a mobile device may not meet for the reasons just explained.

BRIEF DESCRIPTION OF THE DRAWINGS

FIGS. 2A and 2B show an external controller and the manner in which it communicates with the IPG in accordance with the prior art.

FIGS. 7A-7F show identification and characterization of software tasks running in the mobile device as valid, suspendable, or terminable in accordance with an embodiment of the present invention.

DETAILED DESCRIPTION

The inventor has devised solutions to overcome the problems mentioned previously. As discussed in detail below, the inventor discloses techniques for initializing a commercially-available mobile device into a rule-compliant and safe external controller for an implantable medical device. In particular, a Medical Device Application (MDA) operates on the mobile device to temporarily configure it into a known secure configuration for use as an external controller, and to prevent operation of the mobile device inconsistent with this function. In particular, the MDA operates to (1) disable or reconfigure hardware modules, and/or (2) terminate or suspend software tasks, that might corrupt operation of the mobile device as an external controller. The MDA in one embodiment comprises an application ("app") that the patient can download onto his mobile device from the Internet or other network using standard means, which the patient can run to initialize the mobile device into the known secure configuration. The MDA also preferably provides an MDA graphical user interface to allow a user to communicate with the implantable medical device using the now-secure mobile device. After using the mobile device to communicate with the implantable medical device, the MDA can be exited and the mobile device returned to its original configuration.

In another embodiment, the MDA modifies the booting process of the mobile device to initialize it into a known secure configuration. In particular, the modified booting process allows a user to select during the booting process how the mobile device should be configured—either as a normal mobile device or as a medical device for communicating with an IPG—and can take automatic actions to initialize the mobile device into a known secure configuration if the latter is selected. If the user selects use as a medical device, a more-secure medical device kernel can be provided to the mobile device's operating system, which loads into the known secure configuration. Alternatively, the operating system can load with its less-secure normal kernel, but receives the user's selection regarding medical device use during loading of the operating system. If the user selects use as a medical device, the MDA causes the operating system automatically run the MDA described earlier after it boots to initialize the mobile device into the known secure configuration. In either case, the MDA, in addition to modifying the booting process, further preferably automatically provides an MDA graphical user interface after initialization to allow a user to communicate with the implantable medical device using the now-secure mobile device.

Figure 1:
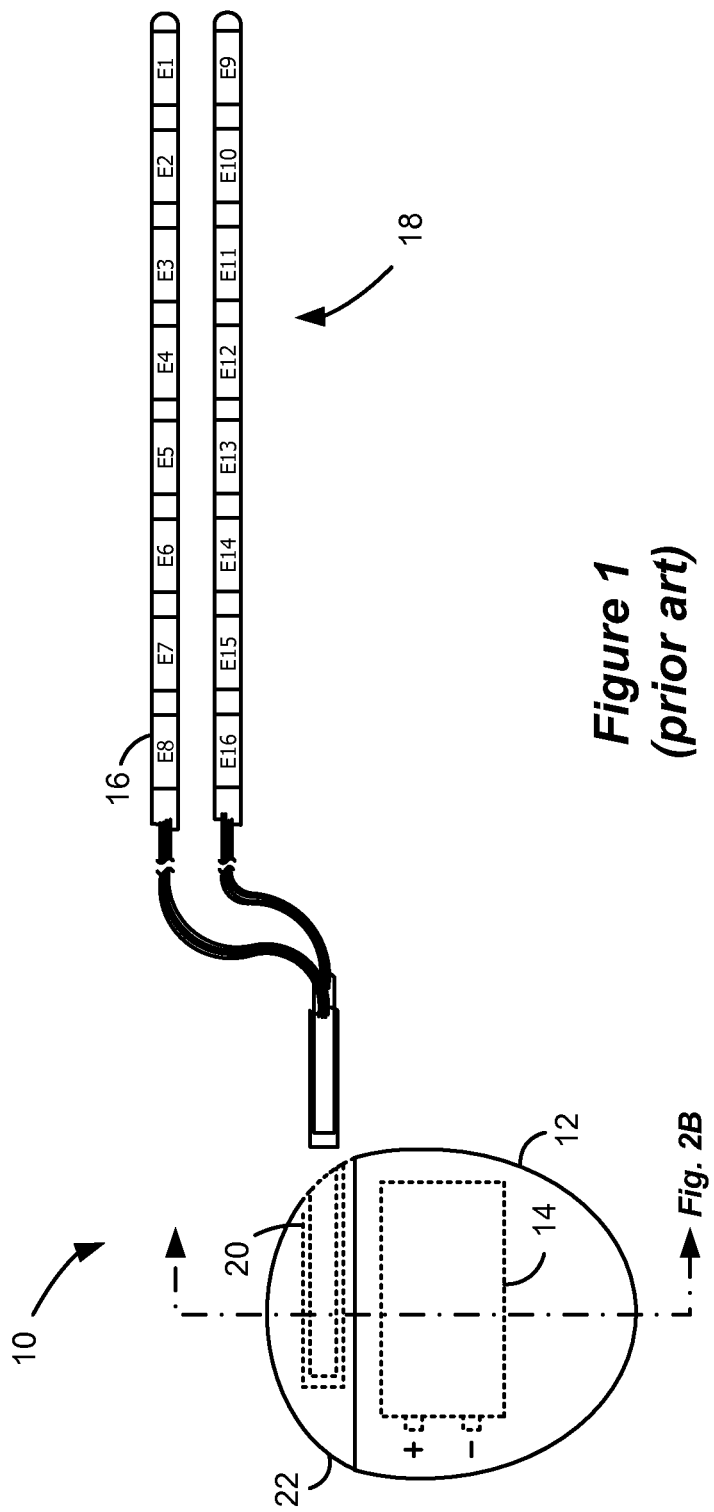
FIG. 1 shows an implantable pulse generator (IPG) in accordance with the prior art.
Figure 3B:
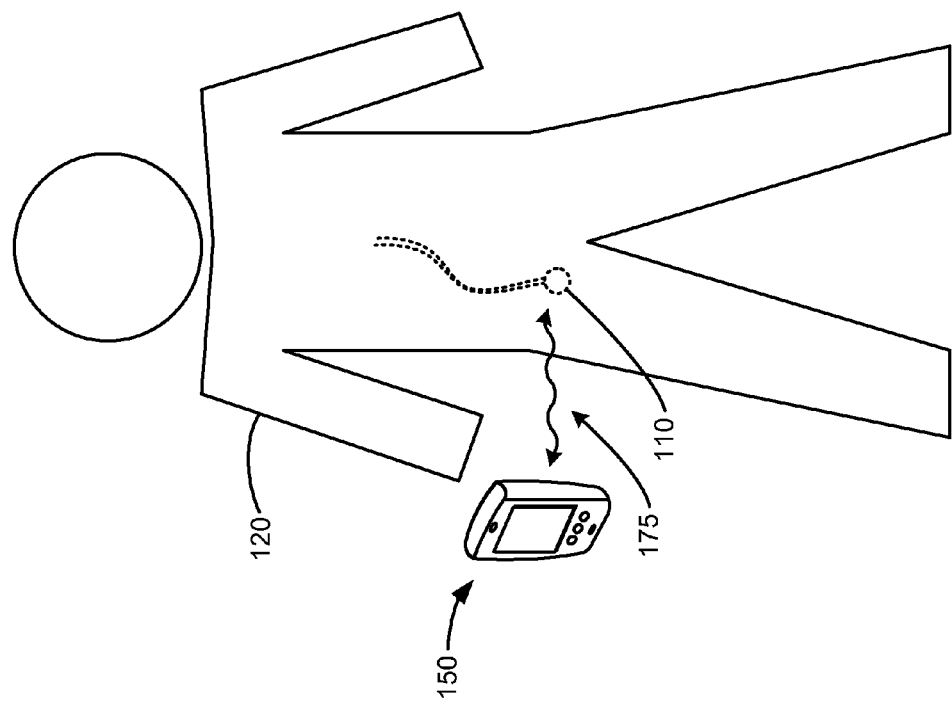
FIGS. 3B-3F show manners in which the mobile device can wirelessly communicate with the IPG.
Figure 3A:
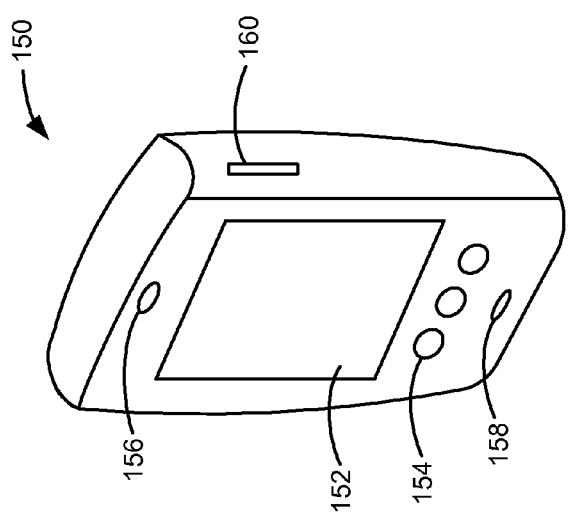
FIG. 3A shows a mobile device in accordance with an embodiment of the present invention.

FIG. 3A shows a mobile device 150, and FIG. 3B shows the mobile device 150 in communication with an IPG 110 implanted in a patient 120, in accordance with an aspect of the invention. The mobile device 150 may be a commercial, multipurpose, consumer device, such as a cell phone, tablet, personal data assistant, laptop or notebook computer, or like devices—essentially any mobile, hand-holdable device capable of functioning as an external controller for an implantable medical device. Examples include the Apple iPhone or iPad, Microsoft Surface, Nokia Lumia devices, Samsung Galaxy devices, or Google Android devices for example.

Among other components and circuitry which will be described in further detail later, the mobile device 150 has a user interface. For example, mobile device 150 may have a display 152 for displaying information. Display 152 may also receive input from a user if it is a touch screen that receives input from a finger or stylus. The mobile device 150 may also have buttons 154 for receiving input from the user, a speaker 156, and a microphone 158. The mobile device 150 may have one or more external ports 160, such as a USB port for example, to connect the mobile device 150 to other devices, to chargers for the mobile device's battery 155 (FIG. 3C), to other computer systems, to memory cards, sticks, or systems, to various dongles, etc.

As noted earlier, mobile devices 150 may be enabled to communicate with other devices using short-range protocols, such as Bluetooth, BLE, NFC, Zigbee, and WiFi, as well as by using long-range cellular telephony protocols. IPG 110 is modified in accordance with an aspect of the invention to directly communicate with the mobile device 150 using one of the mobile device 150's short-range protocols along wireless link 175.

Figure 3C:
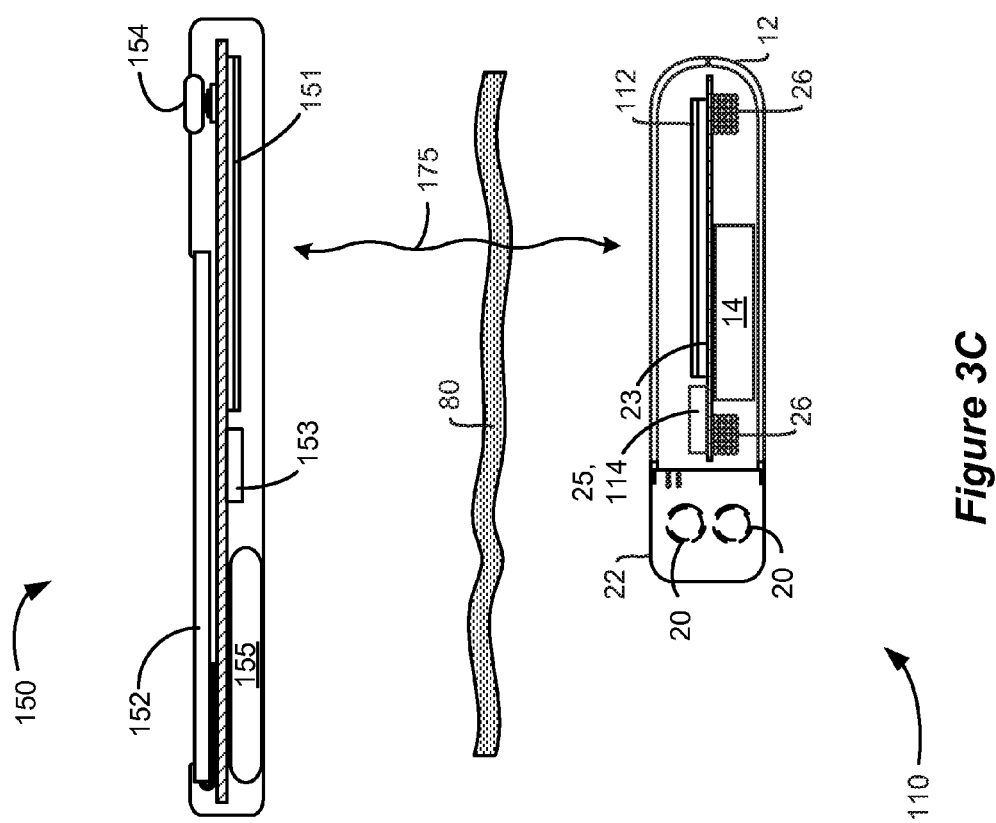

Such means of communication may use an NFC protocol, and as shown in FIG. 3C, the mobile device 150 contains NFC telemetry circuitry 153 (which comprises part of the circuitry used to operate the mobile device 150) and a NFC antenna 151 as is typical, while the IPG 110 is modified from the IPG 10 described earlier (FIG. 2B) to include NFC telemetry circuitry 114 (part of circuitry 25) and a NFC antenna 112. As with the coil-based inductive telemetry scheme discussed for IPG 10 earlier, NFC uses magnetic inductive coupling, and thus NFC antennas 151 and 112 comprise loop antennas. Such loop antennas may be formed as a spiral in a circuit board, such as a flexible Kapton film, as opposed to traditional copper wire windings. Modulation and demodulation of data at the telemetry circuitries 153 and 114 may occur using Miller coding or Manchester encoding for example.

NFC operates within the unlicensed Industrial, Scientific and Medical (ISM) band at 13.56 MHz. NFC is preferred for IPG communications because its lower frequency will not be as attenuated in the patient's tissue 80 as will the higher frequencies used for other short-range protocols. But NFC also operates at shorter distances, at less than 0.2 meters for example. Still, this is suitable as the mobile device 150 can be held relatively close to the IPG 110 during a communication session. Use of NFC to communicate between the mobile device 150 and the IPG 110 though is not strictly necessary, and the IPG 110 can instead include and antenna and circuitry to match other short-range protocols enabled by the mobile device 150.

As shown, in FIG. 3C, the IPG no longer contains a telemetry coil 24 (FIG. 2A), because the communication link 175 between the mobile device 150 and the IPG 110 does not occur using legacy FSK communications. However, this is not strictly necessary, and the IPG 110 could still retain its telemetry coil 24 to allow it to communicate with legacy external controller (FIG. 2A, 50) using FSK.

Figure 3E:
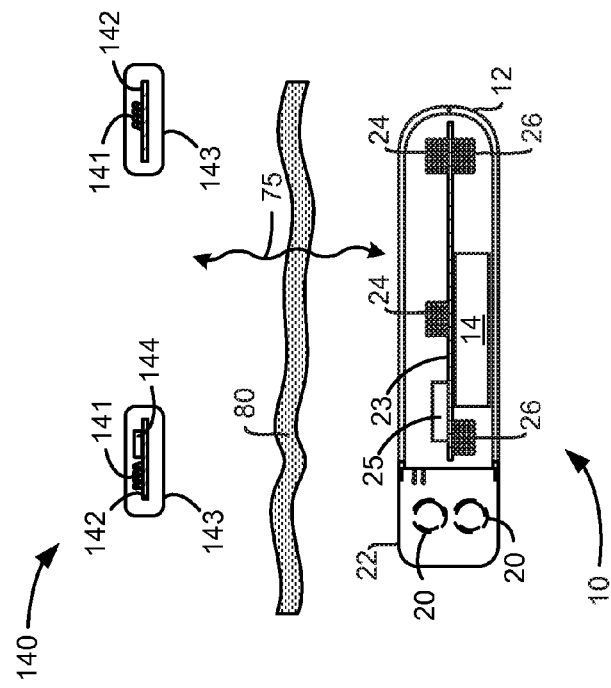
Figure 3D:
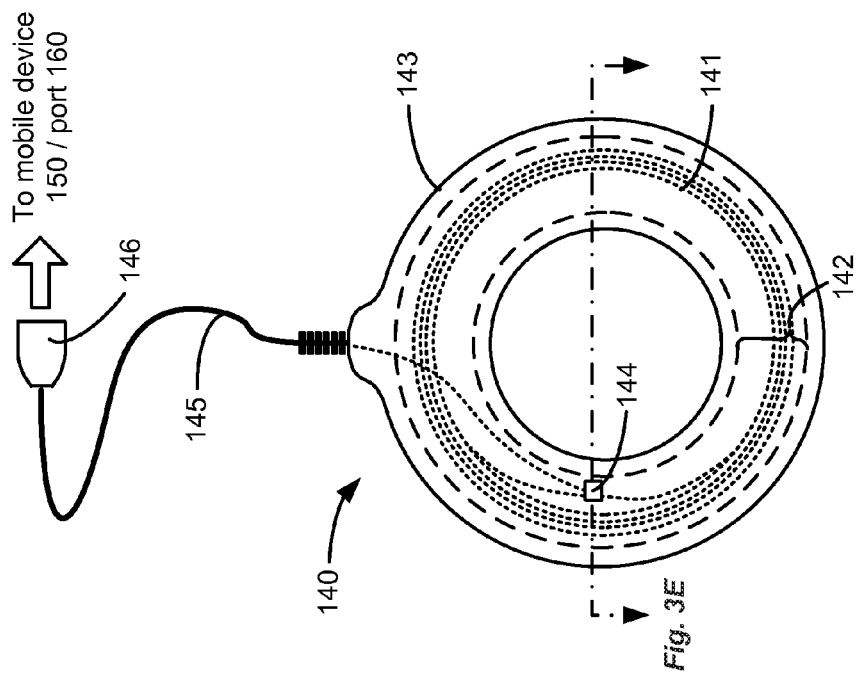

Alternatively, a legacy FSK communication link 75 can be used between the mobile device 150 and an (unmodified) IPG 10 (FIG. 2B), and a first example is shown in FIGS. 3D and 3E. In this example, a telemetry coil assembly 140 is used as an intermediary between the mobile device 150 and the IPG 10. The coil assembly 140 includes a telemetry coil 141 similar to the coil 56 used in the legacy external controller 50 (FIG. 2B), which coil 141 is mounted to a circuit board 142. Also mounted to the circuit board 142 is FSK telemetry circuitry 144, similar to that included as one of the components 59 of legacy external control 50 (FIG. 2B). The telemetry coil 141, circuit board, and FSK telemetry circuitry 144 are contained within a coil housing 143. A cable 145 couples the FSK telemetry circuitry 144 to a connector 146, which couples to a port (e.g., port 160; FIG. 3A) on the mobile device 150. Port 160 can both provide power to the FSK telemetry circuitry 144 and send and receive a string of digital data bits to and from the FSK telemetry circuitry. The FSK telemetry circuitry 144 may include amplifiers and other circuitry to modulate digital data bits sent from the mobile device 150 via port 160 connector 146, and to activate the coil 141 to send FSK modulated data to the IPG 10 via link 75. The FSK telemetry circuitry 144 also includes necessary amplifiers and other circuitry to demodulate FSK modulated data transmitted from the IPG 10 via link 75 and received at coil 141, and to provide such demodulated data as a string of digital data bits to the mobile device 150 via connector 146/port 160. The mobile device 150 can enable port 160 to send and receive the digital data bits when the mobile device 150 is configured for use as a medical device for communicating with the IPG 10, as will be explained in detail later. In this embodiment, the coil assembly 140 can be placed proximate to the IPG 10 (such as in a belt with a pocket), while the mobile device 150 can remain relatively distant from the IPG 10 by virtue of the length of cable 145, which is convenient for the user.

Figure 3F:
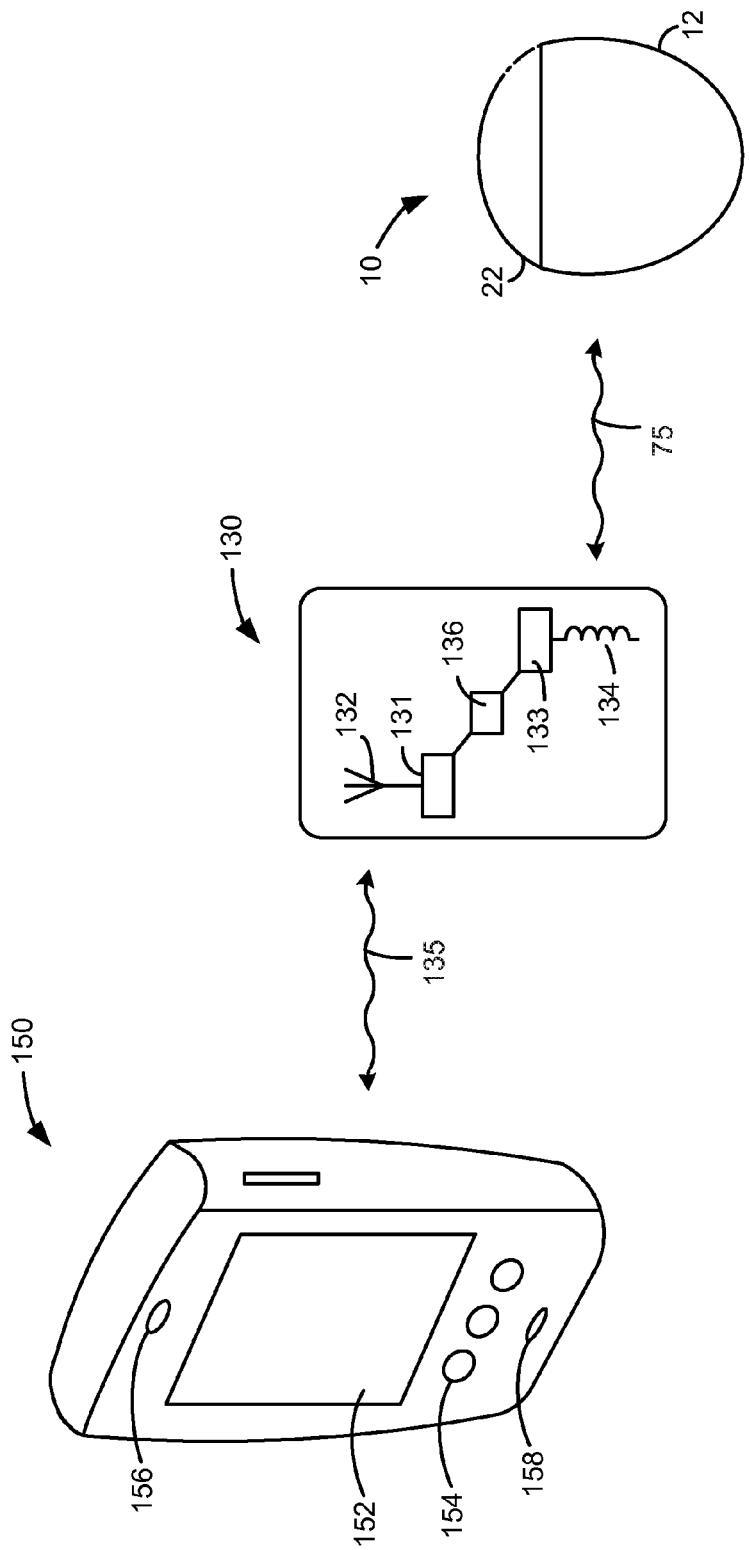

FIG. 3F shows another example of use of a legacy FSK communication link 75 between the mobile device 150 and an (unmodified) IPG 10 (FIG. 2B), in which an intermediary bridge 130 is used, which is disclosed in U.S. Patent Application Publication 2002/0215285, and with which the reader is assumed familiar. The bridge 130 wirelessly communicates with the mobile device 150 via link 135 via a short-range protocol supported by the mobile device, and includes telemetry circuitry 131 and an antenna 132 operable with this short-range protocol. The bridge 130 also wirelessly communicates with the IPG 10 using FSK telemetry via link 75, and includes FSK telemetry circuitry 133 and coil 134. Control circuitry 136 intervenes between the two telemetry circuitries 131 and 133 to control bi-directional communications. Thus, data wirelessly transmitted from the mobile device 150 via link 135 is demodulated at short-range telemetry circuitry 131, and sent to control circuitry 136 which may buffer it, whereafter it is sent to FSK telemetry circuitry 133 where it is modulated and transmitted to the IPG 10 via FSK link 75. Wireless FSK data from the IPG 10 is similarly converted at the bridge 130 to the short-range protocol and transmitted to the mobile device 150 via link 135. In this embodiment, the bridge 130 can be placed proximate to the IPG 10 (such as in a belt with a pocket), while the mobile device 150 can remain relatively distant from the IPG 10 by virtue of the operable distance of the short-range protocol used for link 135, which again is convenient.

Other means for either directly, or indirectly via an intermediary, enabling communications between a mobile device 150 and an IPG or other implantable medical device could be used as well, and the foregoing means merely provide examples.

In accordance with an aspect of the invention, a medical device application (MDA) is used to initialize the mobile device 150 into a known secure configuration allowing it to operate as an FDA-compliant medical device able to communicate with a patient's IPG or other implantable medical device using any of the means described above (FIGS. 3B-3F). As will be explained in detail below, the MDA initializes the mobile device in this fashion by disabling or reconfiguring certain hardware modules, and/or by suspending and/or terminating software tasks, that could potentially corrupt its operation as a medical device. Once the mobile device 150 is initialized, the MDA preferably further provides an MDA graphical user interface to allow a user to communicate with the IPG—for example, to send or adjust an IPG therapy setting and/or to receive data from the IPG. Although the initialization and communication functions are preferably integrated in the MDA, the MDA may merely provide for mobile device initialization, or the MDA could comprise separate applications for initialization and communication.

Different types of mobile devices run on different hardware platforms and with different operating systems. As such, different mobile devices may require different MDAs customized to that operating system or hardware platform. Additionally, different MDAs may be needed in light of the capabilities of the implantable medical device and the therapy it provides. For example, if the implantable medical device is an IPG, the MDA will provide a suitable graphical user interface for communicating with that device, such as providing options to send or adjust stimulation therapy settings. A suitable MDA is likely (but not necessarily) provided to a patient by the manufacturer of the implantable medical device, although the MDA could be downloaded to the mobile device 150 from a number of sources, such as a manufacturer's website or an app store that supports applications written for the operating system of the patient's mobile device 150.

Figure 4:
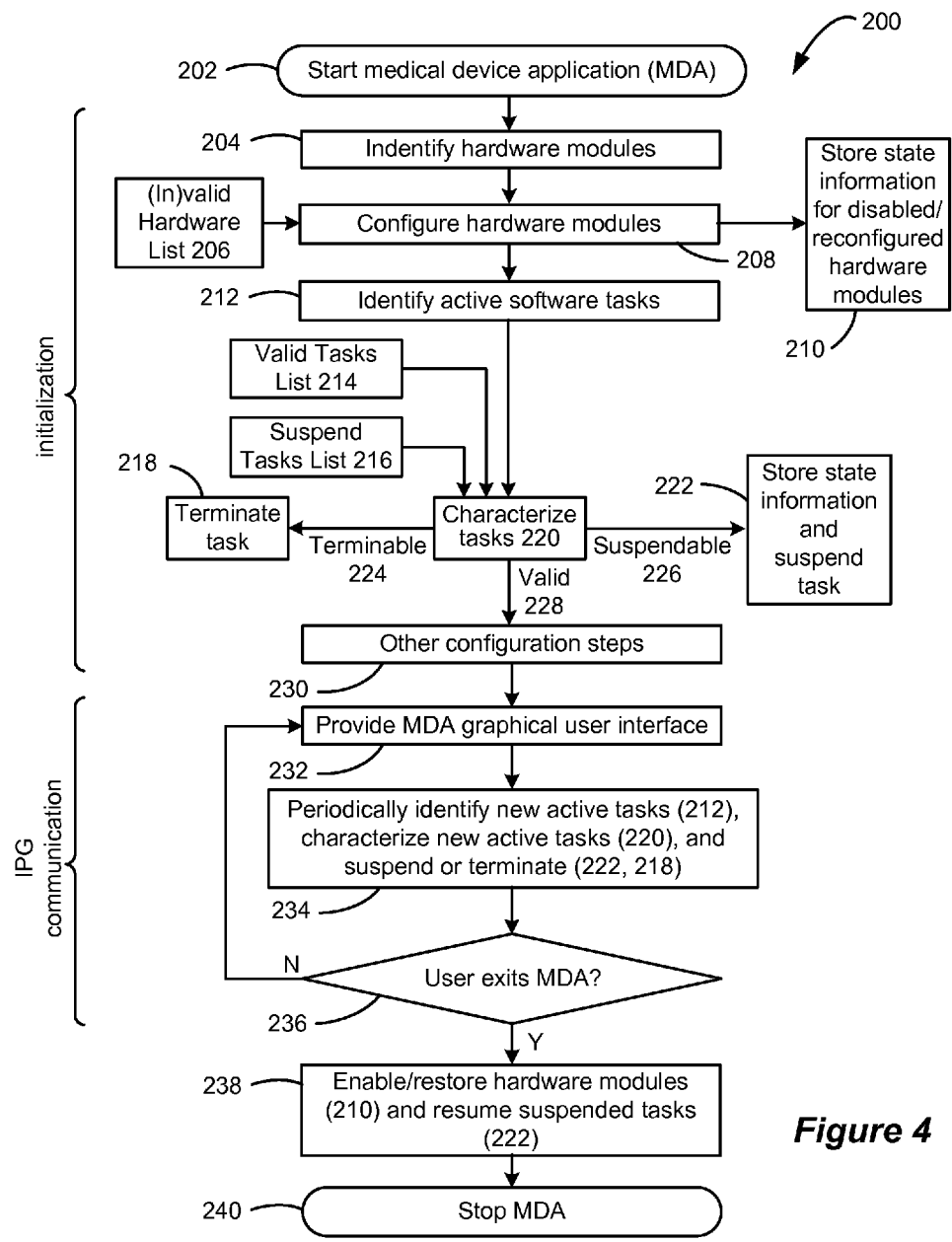
FIG. 4 shows a flow diagram of the medical device application (MDA) in accordance with an embodiment of the present invention.

A first embodiment of an MDA 200 is shown in the flow chart of FIG. 4. The MDA 200 preferably comprises an application ("app") that the patient can download onto his mobile device and run to initialize the mobile device into the known secure configuration. After initialization, the MDA 200 preferably also provides an MDA graphical user interface to enable communications between the mobile device 150 and the IPG as explained further below.

When a user wants to use mobile device 150 to communicate with the IPG, he executes the MDA 200 (202) in any number of ways. In one embodiment shown in FIG. 5, the mobile device provides a graphical user interface 197, in which the MDA 200 is displayed as an icon and is selectable by the user in typical fashion. Icons for other downloaded applications 196 that the user can select may also be displayed. Such other applications 196 as well as other software tasks may be running in the mobile device 150 when the MDA 200 is started, and are addressed by the MDA as explained in detail below.

Once executed, the MDA 200 implements an initialization algorithm (e.g., steps 204-230) to initialize the mobile device 150's hardware and software into a known secure configuration to render it suitable for use as a medical device. Essentially, the initialization algorithm attempts to configure the mobile device 150 into a dedicated external medical device akin to dedicated external controller 50 discussed in the Background. As will be seen, such configuration of the mobile device 150 is only temporary, and the normal configuration of the mobile device 150 can be restored by the MDA 200 when it stops executing.

Starting with the hardware, the MDA 200 first identifies the hardware modules in the mobile device 150 (204). The MDA 200 can identify hardware modules in any number of ways, depending on the operating system being used in the mobile device 150. For example, many operating systems used in mobile devices 150 provide a device manager or like programs that can be used to identify hardware modules in the device, and the MDA 200 may thus use such pre-existing programs at this step. Alternatively, the MDA 200 may comprise a custom device manager, which might be desirable if the operating system lacks programs to identify hardware modules with sufficient particularity. Preferably, identification of hardware modules at this step would additionally include identification of any hardware modules that are coupled to the mobile device, such as at port 160 (FIG. 3A) for example. "Hardware modules" include hardware or circuit blocks, integrated or non-integrated circuits, systems-on-a-chip (SoC), circuit blocks within an integrated circuit, peripheral devices, input/out devices, either individually or in combination, and including their subcomponents and software if any, i.e., any structure operable in the mobile device 150.

The MDA 200 may additionally at step 204 authorize the mobile device to communicate with the IPG, as discussed in U.S. Patent Application Ser. No. 61/832,076, filed Jun. 6, 2013.

Next, the MDA 200 configures the hardware modules in the mobile device 150 into a known secure configuration (208). During this step, the MDA 200 disables or reconfigures certain hardware modules that are not necessary to its functions, as further described with respect to FIGS. 6A-6B.

Figure 6B:
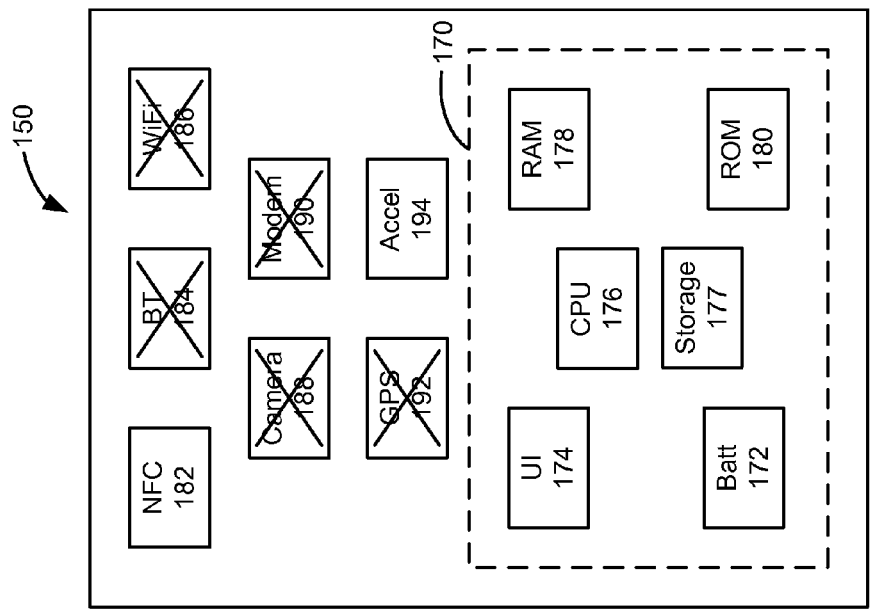
FIGS. 6A and 6B show hardware modules in the mobile device that are disabled by the MDA in accordance with an embodiment of the present invention.
Figure 6A:
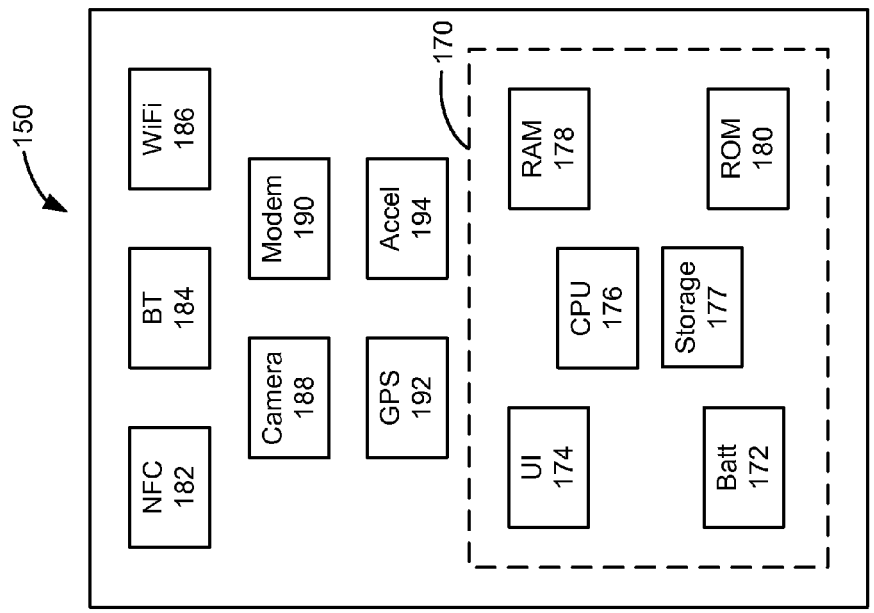

FIG. 6A shows exemplary hardware modules for a mobile device 150 such as a mobile cell phone. A mobile device 150 typically comprises core hardware modules 170 central to the operation of the mobile device 150, such as a battery module 172, user interface modules 174 (enabling functionality of the display 152, buttons 154, speaker 156, and microphone 158 of FIG. 3A), a processor module 176, non-volatile storage 177, random access memory (RAM) 178, and read only memory (ROM) 180. Non-volatile storage 177 may comprise a hard drive for storing the operating system, various applications and data, etc. The ROM 180 may include boot code that executes when the mobile device 150 is initially powered or reset, and may be separate from or included as part of the processor module 176. Initialization of the mobile device 150 as a medical device by modifying the booting process of the mobile device 150 is discussed further below. It should be noted that the processor module 176 may comprise any processing circuitry (e.g., a microprocessor or a microcontroller), may comprise more than one processing core, and may be spread among multiple interconnected hardware modules.

Mobile device 150 typically also includes other non-core hardware modules such as a near-field communication (NFC) module 182, a Bluetooth module 184, a WiFi module 186, a camera module 188, a cellular modem module 190, a GPS module 192, and an accelerometer module 194, to name just a few obvious examples. Such non-core hardware modules are typically controlled by software tasks running in the processor 176.

Some of the non-core hardware modules may not be needed by the MDA 200 and are thus disabled by the MDA to make the mobile device 150 more secure and to remove means by which the mobile device 150 can be corrupted. FIG. 6B shows an example of hardware modules that might be disabled by the MDA 200. For example, if the mobile device 150 is to communicate with the IPG using NFC module 182, Bluetooth module 184 and WiFi module 186 would be disabled by the MDA 200, as shown in FIG. 6B. By contrast, if the mobile device 150 is to communicate with the IPG using Bluetooth module 184, NFC module 182 and WiFi module 186 would be disabled. Non-core hardware modules such as the camera module 188, cellular modem module 190, GPS module 192, and accelerometer module 194 may also not be needed and may be disabled by the MDA 200, particularly if the MDA 200 is only designed to communicate with the IPG. Which hardware modules are disabled by the MDA 200 depends on the manner in which the MDA is designed to operate. For example, if the MDA 200 is designed to detect tremors in a Parkinson's patient having a DBS implant, and to control stimulation based on detected tremor, the MDA 200 may not disable the accelerometer module 194, as shown in FIG. 6B.

The MDA 200 may also store state information for the hardware modules it has disabled (210). This will allow the MDA 200 to re-enable such hardware modules upon exiting the MDA, as discussed further below.

Disabling of hardware modules in the mobile device 150 at step 208 can be assisted through the use of a Valid Hardware List 206 provided by the MDA 200, as shown in FIG. 4. The MDA 200 can compare the identified hardware modules (204) with those on the Valid Hardware List 206, and disable the identified hardware modules that do not match. List 206 could alternatively comprise an Invalid Hardware List, and thus will disable identified hardware modules matching those on this list, leaving other hardware modules active by default. Such lists can be updated as the MDA 200 is periodically updated via the Internet for example. Rules may also be used to determine which hardware blocks to disable, which rules may depend on monitoring the actual operation of the hardware blocks to gauge their potential to conflict with or corrupt the MDA 200.

One skilled will realize that the MDA 200 can disable the non-core hardware modules in any number of ways. For example, the processor 176 that executes the MDA 200 can send control signals to such non-core hardware modules instructing them to suspend operation or enter a power-down mode. Alternatively, the control signals sent from the processor 176 can cut power to the non-core hardware modules.

Hardware modules can be configured at step 208 in manners other than disabling or enabling them. For example, the MDA 200 can also reconfigure a given hardware module by causing the processor 176 to send control signals or to reprogram that hardware module to alter its function in a more secure manner less likely to corrupt MDA operation. Should this occur, state information would be stored (210) to allow the MDA 200 to restore the affected hardware module its original configuration upon exiting the MDA. The (In)valid Hardware List 206 discussed above can be useful in deciding which hardware modules may need to be reconfigured.

After configuring the hardware, MDA 200 next configures the software in the mobile device 150. This process starts by identifying foreground and background software tasks running in the mobile device 150 (212). An example list of identified tasks 213 is shown in FIG. 7A. The MDA 200 can identify active tasks in any number of ways, depending on the operating system being used in the mobile device 150. For example, many operating systems used in mobile devices 150 provide a task manager or like programs that can be used to identify active tasks, and the MDA 200 may thus use such pre-existing programs at this step. Alternatively, the MDA 200 may comprise a custom task manager, which might be desirable if the operating system lacks programs to identify tasks with sufficient particularity. "Tasks" include applications, programs, processes, services, or threads, either individually or in combination, and including their subcomponents, i.e., any software operable in the mobile device 150.

Next, the MDA 200 characterizes the tasks (220), which it does with the assistance of a Valid Task List 214 and a Suspend Task List 216 included with the MDA, which are illustrated in FIGS. 7B and 7C respectively.

The Valid Tasks List 214 of FIG. 7B comprises tasks that are either needed by the MDA 200 after initialization and/or are trusted to not corrupt the operation of the MDA. Thus, the Valid Tasks List 214 may include tasks relating to the system clock (which may be necessary to allow the MDA 200 to time stamp data during its operation), antivirus detection and correction, the user interface modules (which the user will need to access the functionality of the MDA 200 after initialization), the MDA itself, the task manager (which may continue to run even after initialization, as explained below), and other tasks. These are just some simple examples for illustration purposes; which tasks should be deemed valid in an actual MDA implantation will depend on the desired operation of the MDA as well as designer preferences.

The Suspend Tasks List 216 of FIG. 7C comprises tasks that are not needed by the MDA 200 and hence can be suspended, but are trusted and desirable to resume in the mobile device 150 after exiting the MDA to convenience the user. Thus, the Suspend Tasks List 216 may include tasks relating to e-mail and e-mail synchronization, software updates, alarm clocks, telephony functions, e-mail programs, and other tasks. Again, these are just some simple examples of suspendable tasks.

The tasks in the Identified Task List 213 (FIG. 7A) are characterized at step 220 by comparing the identified tasks to those appearing in the Valid Tasks List 214 (FIG. 7B) and the Suspend Task List 216 (FIG. 7C), with the result that the identified tasks are characterized as valid tasks 228 (FIG. 7D), suspendable tasks 226 (FIG. 7E), and terminable tasks 224 (FIG. 7F). Valid tasks 228 in FIG. 7D comprise those appearing in both the Identified Task List 213 (FIG. 7A) and the Valid Task List 214 (FIG. 7B), and likewise suspendable tasks 226 in FIG. 7E comprise those appearing in both the Identified Task List 213 and the Suspend Task List 216 (FIG. 7B).

The terminable tasks 224 in FIG. 7F essentially comprise all other remaining tasks, which by default would include those that are not are trusted or which can be easily re-run by the user without inconvenience on the mobile device 150 after exiting the MDA 200. Examples of such terminable tasks 224 in FIG. 7F include tasks relating to music players, video games, and mapping programs—tasks that a user would presumably not mind re-running after using the MDA 200. Other terminable tasks 224 may comprise tasks that cannot be trusted. For example, Internet browsing applications, or push service applications requiring Internet access, provide potential communication routes for data which might corrupt operation of the MDA 200. In short, MDAs not requiring Internet or other network access will likely terminate all tasks permitting such access. However, other MDAs may require network access, for example, by reporting therapy or IPG data to the Internet for review or processing, in which case such tasks may merely be suspendable and resumed upon exiting the MDA 200. Again, other examples of terminable tasks 224 are possible, and terminal tasks will vary based on the desired operation of the MDA and designer preferences.

Thereafter, and referring again to FIG. 4, the terminable tasks 224 are terminated (218) by the MDA 200, which can be done with the assistance of the task manager referenced earlier. Suspendable tasks 226 will eventually be resumed, and so their state information is stored before these tasks are suspended (222). As one skilled in the art will realize, storing the state information will allow the MDA 200 to resume the suspended tasks in the state they existed at the time of suspension. Again, the task manager can assist in storing state information and in suspending such tasks. Valid tasks 228 (FIG. 7D) may continue to run during operation of the MDA 200.

It should be noted that configuration of the software can occur in other manners than described above. For example, the MDA 200 can provide a Terminate Task List (not shown), which includes known untrusted tasks and which are used during task characterization to affirmatively terminate those tasks rather than terminating them by default. Tasks can also be characterized without reference to pre-defined lists, such as by the use of rules that review the actual operation of tasks to gauge their potential to conflict with or corrupt the MDA 200. Additionally, tasks may simply be characterized as valid or invalid, with valid tasks being allowed to continue to run, and invalid tasks being terminated. Untrusted or unnecessary tasks may also merely be suspended and resumed later upon exiting the MDA 200, as opposed to being terminated. It should also be noted that the lists or rules used to characterize tasks and to take appropriate actions can be updated as the MDA 200 is periodically updated via the Internet for example.

At this point, the MDA can take other configuration steps (230) to further improve initialization of the mobile device 150 as a medical device. For example, the MDA 200 can register itself with the mobile device 150's operating system with a suitable (e.g., highest) priority to reduce the possibility that other tasks will interfere with MDA operation. The MDA 200 may also partition and protect the memory space it will use to prevent other tasks from accessing MDA data.

The initialization algorithm need not occur strictly in the order presented in FIG. 4. For example, software can be configured first (steps 212-228), with hardware configured later (204-210). Additionally, there may be some degree of overlap between hardware and software configuration. For example, if a particular hardware module was disabled or reconfigured, this may automatically result in the suspension or termination of certain tasks. And suspension of termination of a task may effectively disable or reconfigure a particular hardware module.

The initialization algorithm also need not involve all of the steps described previously. For example, initialization may only configure the hardware (204-210), or only configure the software (212-228), or only take other initialization steps (230), although it is preferable to take all of the disclosed steps to provide a configuration for the mobile device 150 that is as secure as possible.

In any event, once mobile device 150 is initialized by configuring the hardware and software, the result is a mobile device 150 with a known secure configuration that is less vulnerable to corruption, is certifiable with the FDA or other regulatory bodies for use as a medical device, and is ultimately safer for the IPG patient.

Figure 8:
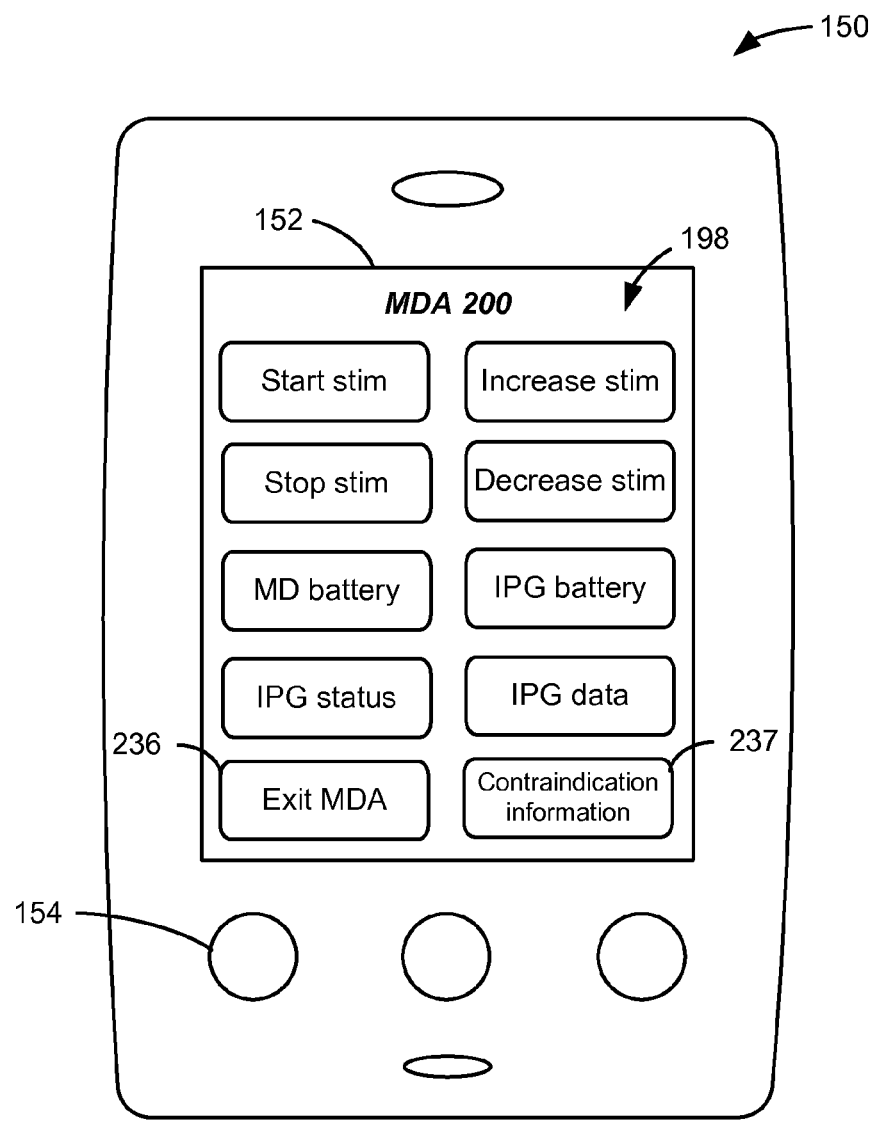
FIG. 8 shows a graphical user interface for the MDA to enable communications between the mobile device and the IPG.

With initialization of the mobile device complete, communications between the mobile device 150 and the IPG may now begin. At this point, MDA 200 (assuming it is not used simply for mobile device initialization) will provide an MDA graphical user interface 198 (232) to allow a user to send or adjust therapy settings for the IPG and/or to receive data from the IPG, as shown in FIG. 8. For example, the display 152 may present options to start or stop stimulation, to increase or decrease the magnitude of stimulation, to check the battery status of the IPG or the mobile device 150, to check the IPG's status, or to review data telemetered from the IPG, etc. Such options may be selectable on the display 152 if it is a touch screen, or the MDA 200 can configure buttons 154 to allow for user control.

MDA 200 may additionally include a selection 237 to provide contraindication information to the patient, similar to the technique disclosed in U.S. Pat. No. 8,588,925, which is incorporated herein by reference. The '925 patent explains that "contraindication information" can be stored in a traditional dedicated external controller, such as the external controller 50 of FIGS. 2A and 2B, allowing such information to be reviewed on the external controller 50 itself, or provided from the external controller 50 (e.g., by cable, by a memory stick, wirelessly, etc.) to another computer device or system and reviewed there (such as a clinician's computer). Such "contraindication information" can comprise information that a patient or clinician might wish to review when assessing the compatibility of a given therapeutic or diagnostic technique or other activity with the patient's implant, such as: the patient or clinician's manuals for the implant system, including the manuals for the implant and any associated external devices (e.g., remote controllers or external chargers); any specific contraindicated therapeutic or diagnostic techniques or activities; contact information for the manufacturer of the implant system or its service representative; clinician contact information, for example the contact information of the clinician who implanted the implant, or another clinician having information relevant to the use of particular therapeutic or diagnostic techniques or other contraindicated or compatible activities; clinician instructions regarding therapeutic or diagnostic techniques or activities compatible with or contraindicated by the patient's implant; patient history or patient records relevant to a particular therapeutic or diagnostic techniques or activities compatible with or contraindicated by the patient's implant; etc. "Contraindication indication" can also indicate procedures or activities that are compatible with the patient's implant as well as those that are prohibited, at least to some conditional degree. Similar to the teaching of the '925 patent, contraindication information may be stored in the mobile device 150, and via selection 237 may be shown on its display 152 or provided from the mobile device 150 (e.g., wirelessly, using its short-range RF communication means as explained earlier) to another computer device or system.

Referring again to FIG. 4, the MDA 200 may during the communication session with the IPG optionally periodically run aspects of the initialization algorithm (steps 204-230), in particular to monitor and if necessary configure the software in the mobile device 200. This is preferable to ensure that, despite previous initialization efforts, new software tasks that were perhaps unforeseen or unknown do not corrupt MDA 200 operation. In this regard, the MDA 200 can periodically identify new active tasks, characterize them, and if necessary suspend or terminate them (234) in the same manners discussed previously (steps 212-228). The MDA 200 can also periodically configure the hardware modules as described earlier (204-210). The need to revisit configuration of the hardware after initialization may not be as strong, although this may still be prudent, especially in the off chance that a software task has re-enabled or reconfigured a particular hardware module.

Once a user is finished communicating with the IPG, he can exit the MDA 200 (236), as shown in FIGS. 4 and 8. The MDA 200 may also automatically be exited without user intervention upon the occurrence of certain actions or inactions. At this point, and before the MDA 200 actually stops executing in the mobile device 150 (240), the MDA will restore the mobile device to return it (as best it can) to its original configuration prior to running the MDA (238). In this regard, previously-disabled or reconfigured hardware modules can be enabled or restored using the state information stored earlier (210), and previously-suspended software tasks can be resumed using the state information stored earlier (222). Thereafter, the MDA 200 can stop executing (240), allowing normal consumer use of the mobile device 150. That is, the operating system provides the mobile device user interface 197 (FIG. 5), and the user can freely choose to use other downloaded applications 196.

Alternatively, the MDA 200 at step 240 could cause the mobile device 150 to restart (e.g., to power down and reboot) upon exiting, which might be necessary for example if actions taken by the MDA 200 make it difficult or impossible to restore the configuration of mobile device 150. Should the MDA 200 be specifically designed to always restart the mobile device 150 upon exit, it would be unnecessary to store state information (210, 222), and those steps could be omitted.

Figure 5:
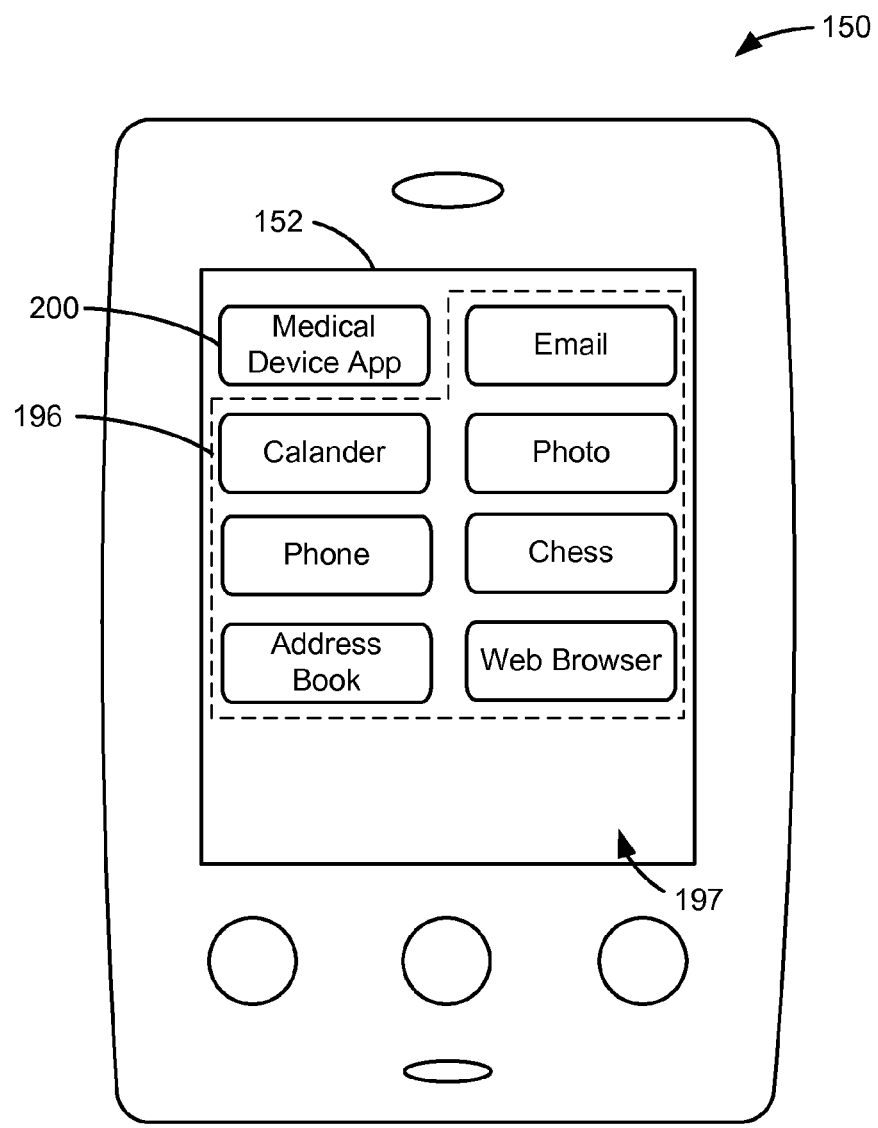
FIG. 5 shows an exemplary manner in which the MDA can be selected via a mobile device graphical user interface.

The MDA need not strictly comprise an application that is run after the operating system of the mobile device 150 is fully loaded and is providing the mobile device graphical user interface 197 to allow user input to the mobile device (FIG. 5). In other embodiments, the MDA can automatically begin executing on a mobile device 150 during its booting process after it is powered on or restarted, and can modify the booting process allows a user to select during the booting process how the mobile device 150 should be configured—either as a normal mobile device or as a medical device for communicating with an IPG. The MDA can take automatic actions to initialize the mobile device into a known secure configuration if the latter is selected.

Figure 9A:
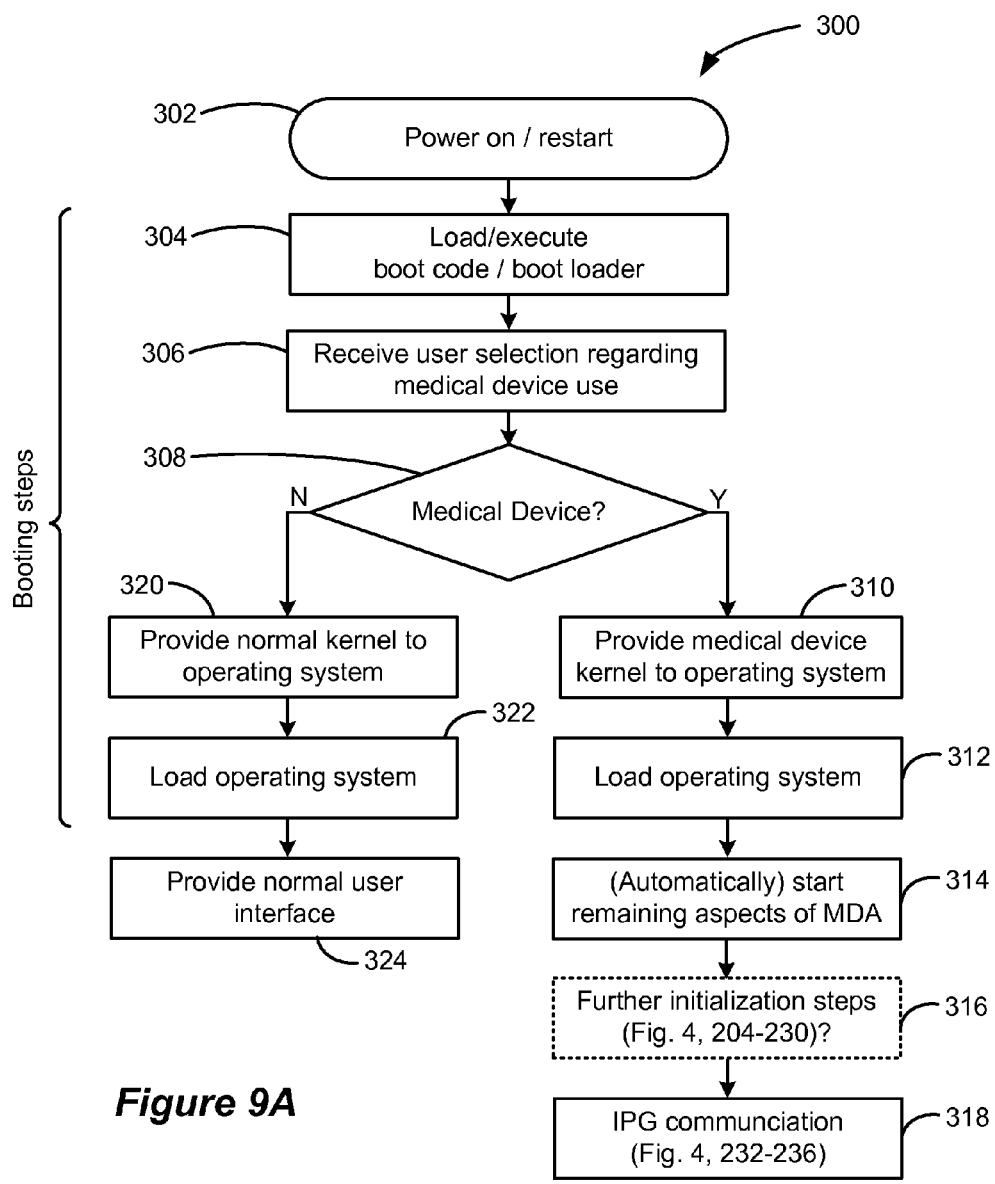
FIGS. 9A and 9B show alternative flow diagrams for the medical device application (MDA) that modify the booting process of the mobile device.

FIG. 9A illustrates a first embodiment 300 of an MDA that modifies the booting process 300, which involves modifying the kernel provided to the operating system of the mobile device 150 based on a user's selection regarding use of the mobile device as a medical device. Once the mobile device 150 has been powered on or restarted (302), certain booting steps are undertaken that implicate some of the hardware modules of FIG. 6A.

First, the processor 176 will load the boot code from ROM 180 to RAM 178 and execute it (304). Such boot code includes a boot loader, which later in the boot process provides an appropriate kernel to the operating system of the mobile device 150. The boot code/boot loader will also perform basic configuration of the mobile device 150, such as to activate certain user interface modules 174, or to provide a boot screen to the display 152 of the mobile device. Such basic configuration steps may reference data stored independently of the boot code loader. For example, the kernel or data for the boot screen may reside in the non-volatile storage 177 of the mobile device and retrieved during execution of the boot code/boot loader, or such data may comprise a portion of the boot code/boot loader.

The booting process of MDA 300 under control of the boot loader next receives a selection from the user whether it should boot normally or as a medical device for communicating with the implant (306), prior to loading the operating system of the mobile device. This is desirable, as a user will obviously not always want to use the mobile device 150 as a medical device every time the mobile device 150 is powered or restarted, and therefore may wish to use the mobile device 150 normally without medical device restrictions.

Such selection may be provided to the booting process in any number of ways. For example, and as shown in FIG. 9C, the booting process may provide medical device selection graphical user interface 199 as a boot screen that provides user selectable options to either run the mobile device normally (e.g., as a phone) or as a medical device. Buttons 154 may also be used to provide this selection. For instance, pressing a button or combination of buttons while powering or restarting the mobile device 150 may indicate that the user intends to use the device as a medical device. The user might also insert hardware (e.g., a dongle) into a port 160 of the mobile device 150 when desiring to use the mobile device 150 as a medical device, and the booting process can check for the presence of such hardware. Such hardware at port 160 may also comprise data the boosting process can use to initialize the mobile device as a medical device, or to initialize it in a particular way depending either on the particulars of the mobile device 150 or the IPG or other implantable medical device.

If medical device use is indicated (308), the boot loader will provide a medical device kernel to the operating system (310) provided by the medical device application. A kernel, as is well known, causes the operating system during loading to initialize the mobile device 150's hardware and resources, such as the processor 176, memory, and input/output devices, and so the medical device kernel will appropriately causes the operating system to initialize such hardware and resources to render the mobile device 150 secure for medical device use. Thus, when later-run applications make system calls to the operating system as is typical, they will be restricted by the limitations provided by the operating system as modified by the medical device kernel. Such limitations may affect aspects of the mobile device 150 discussed earlier, such as by disabling or reconfiguring certain hardware modules or by suspending and terminating certain software tasks to render the mobile device less susceptible to corruption. The boot code, boot loader, and medical device kernel can be provided by the MDA 300 to implement this functionality, as described further below.

If medical device use is indicated (308), the boot loader may also modify aspects of the normal kernel to include necessary medical-device limitations and provide that modified normal kernel to the operating system, which should also be understood as providing a medical device kernel at step 310. In this regard, the MDA 300 may only provide modifications to the parameters of the normal kernel, which modifications should be understood as a medical device kernel even if what the MDA provides is not a complete kernel.

Thereafter, the operating system with the medical device kernel is loaded until booting is complete (312), at which point the medical device kernel via the operating system has initialized the mobile device 150 into a known secure configuration for medical device use. As such, use of the medical device kernel essentially takes the place of (or supplements) the initialization steps discussed earlier (FIG. 4, 204-230).

At this point, the MDA 300 preferably automatically starts remaining aspects of MDA 300 (314) to allow the user to communicate with the IPG (314). For example, the mobile device 150 may at step 314 automatically provide the MDA graphical user interface 198 (FIG. 8) as described earlier to allow a user to send or adjust IPG therapy or to receive data from the IPG. As such, no other downloaded applications 196 could be selected by the user at this step.

Alternatively, the MDA 300 may require a user selection at step 314 to start remaining aspects of MDA 300. In this regard, the MDA 300 may provide the mobile device graphical user interface 197 (FIG. 5), which requires selection of the MDA to communicate with the IPG, i.e., to bring up the MDA graphical user interface 198 (FIG. 8). The mobile device graphical user interface 197 may include the other downloaded applications 196 that the user can choose to run as discussed earlier. However, these other applications 196 may not work if they employ system calls inconsistent with the limitations of the medical device kernel. The operating system thus might earlier (312) automatically check such other applications 196 for such inconsistency, and display and allow the user to choose only those which will operate consistently with the medical device kernel at step 314. Such other consistent applications 196 would presumably be safe, and raise little risk of MDA 300 corruption. Thus, at least some normal functionality of the mobile device 150 can be accessed prior to communicating with the IPG at this step, as the loaded medical device kernel has rendered the mobile device 150 secure for medical device use.

Although the booting steps 304-312 initialize the mobile device 150 into a known secure configuration, further initialization steps can be undertaken (316), such by performing certain aspects of the initialization algorithm described earlier (FIG. 4, 204-230), to further bolster security of the mobile device 150. However, given the security provided by the medical device kernel, this may not be necessary. This optional step 316 could also proceed step 314, or come both before and after step 314. Thereafter, the user can operate the mobile device 150 to communicate with the IPG via the MDA graphical user interface (FIG. 8) (318). The MDA 300 may monitor or alter configuration of hardware modules and software tasks during this step 318 as described earlier (FIG. 4, 232-236).

When the user is finished communicating with the IPG and wishes to use the mobile device 150 normally, the user can exit the MDA 300, as provided for in the MDA graphical user interface 198 (FIG. 8). However, because the medical device kernel is loaded, exiting MDA 300 will either power down or restart the mobile device. The user can then select to user the mobile device normally (306). Alternatively, upon exiting MDA 300, the operating system can provide the mobile device graphical user interface 197 (FIG. 5) to allow the user to select other downloaded applications 196. However, as noted earlier, these other applications 196 may not work with the medical device kernel that is currently loaded. The operating system thus might at this point display and allow the user to choose only those other applications which will operate consistently with the medical device kernel, which again are presumably safe.

If medical device use is not indicated (308), the MDA 300 allows the boot loader to provide a normal kernel to the operating system (320) and the operating system loads (322) until booting is completed, which will configure the mobile device 150 without medical device limitations, as a normal cell phone in this example. Thus, the operating system will provide the mobile device graphical user interface 197 (FIG. 5) (324) to allow the user to select other downloaded applications 196, although an icon for the MDA may not be present, consistent with the selection provided earlier (306).

The MDA 300 can be provided to a patient in any number of ways as discussed above, and may be downloaded onto the mobile device 150 from the Internet or other network using standard means. The MDA 300 may comprise an executable file, or patch, which includes the boot code, boot loader, and/or the medical device kernel, and when executed will make the necessary changes to the boot code/boot loader of the mobile device and provide the medical device kernel to the mobile device 150 to implement the functionality of MDA 300 as described above. MDA 300 can also include at least some or all of the aspects of MDA 200, such as the MDA graphical user interface 198 (FIG. 8) (318) and aspects dealing with initialization (316). When the patch is executed, these aspects of MDA 200 may also be automatically installed and run at appropriate times as discussed above. Alternatively, these aspects of MDA 200 may be separately downloaded (e.g., as an "app") separate from the patch.

Figure 9B:
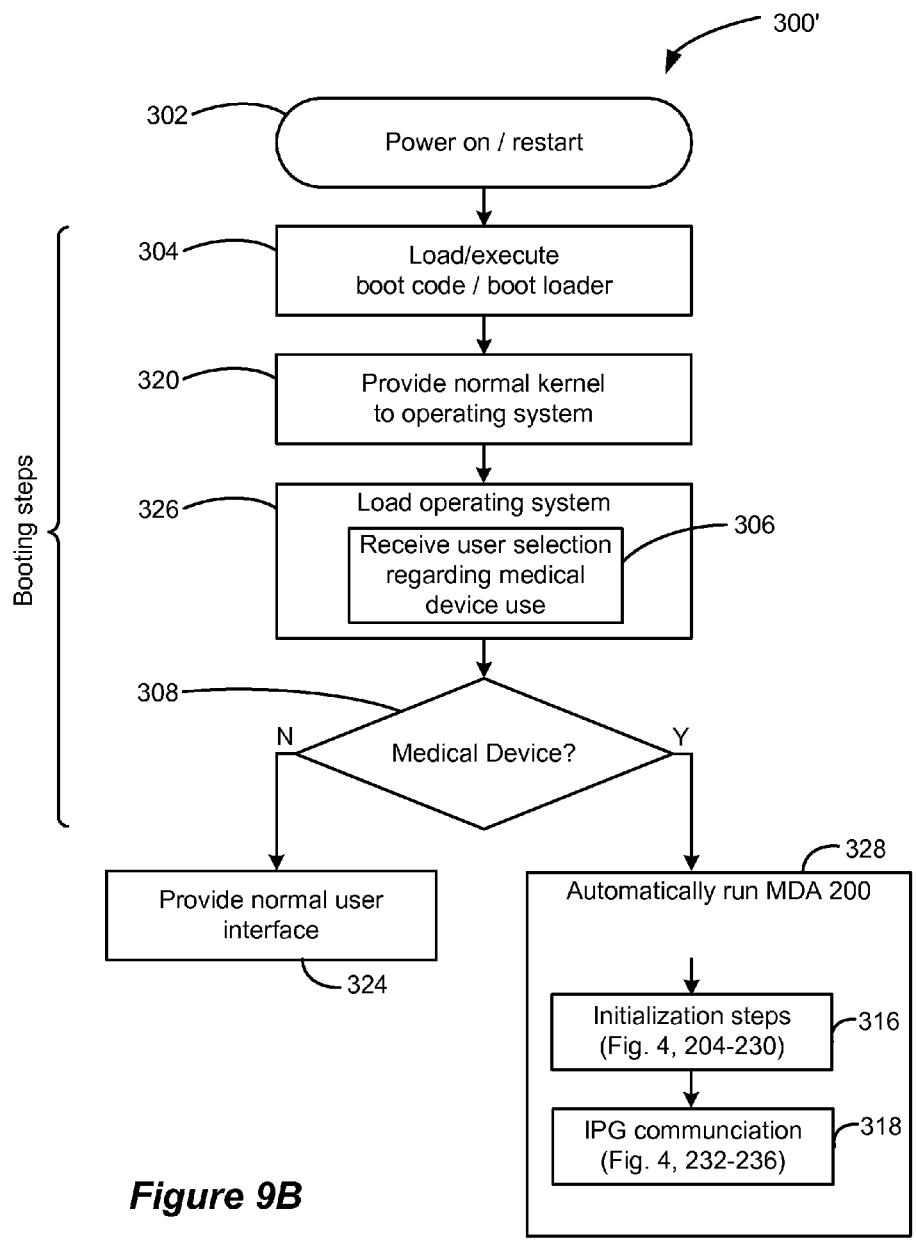
Figure 9C:
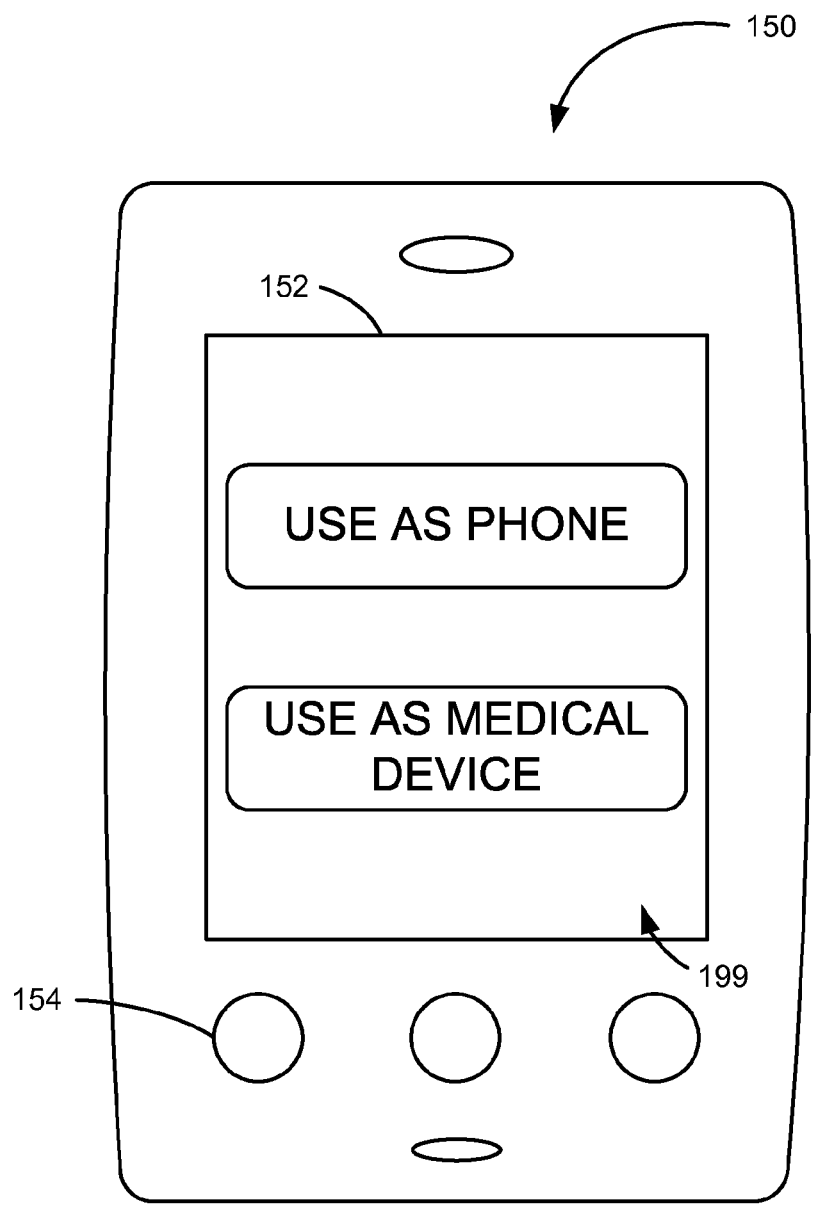
FIG. 9C shows a medical device selection graphical user interface used to modify the booting processes of FIG. 9A and 9B.

FIG. 9B shows a modified MDA 300' in which the operating system begins loading with its less-secure normal kernel, but receives the user's selection regarding medical device use during its loading process. If the user selects use as a medical device, the operating system automatically runs the MDA described earlier (FIG. 4) after it boots to initialize the mobile device into the known secure configuration.

As shown, after powering or restarting the device (302), the boot code/boot loader is loaded and executed (304), the normal kernel is provided to the operating system (320), and the operating system begins loading (326). During loading of the operating system, either as a first step, the last step, or in between, the MDA 300' receives the user selection 306 indicating whether use of the mobile device 150 normally or as a medical device is desired. As described earlier, this selection can be received in a number of ways. However, providing the medical device selection graphical user interface 199 (FIG. 9C) during loading of the operating system is preferred in this example, as loading of the operating system can make generation of such a user interface easier. For example, the operating system can almost fully load at this step, providing the user interface 199 and receiving the user selection as a last booting steps.

If medical device use is indicated by the selection (308), there is little reason in MDA 300' to allow a user the option to select other downloaded applications 196 or access other general functionality of the mobile device 150. After all, the user has already indicated his desire to use the mobile device 150 as a medical device, and no actions have been taken at this point to render the mobile device secure for medical device use. Thus, after loading, the MDA 300' causes the operating system to automatically start executing further aspects of the MDA 300' to render the mobile device 150 secure (328). As shown in FIG. 9B, this can comprise automatically running the MDA 200 described earlier, including automatically running the initialization algorithm described earlier (FIG. 4, 204-230) to render the mobile device 150 secure (316), and communicating with the IPG via MDA graphical user interface 198 (318) (FIG. 4, 232-236).

When the user is finished communicating with the IPG and wishes to use the mobile device 150 normally, the user can select to exit the MDA 300', as provided for in the MDA graphical user interface 198 (FIG. 8). In this example, the mobile device's normal kernel has been loaded (320), and thus there is no need to power down or restart the mobile device. Instead, upon exiting MDA 300', the mobile device 150 provides the mobile device graphical user interface 197 (FIG. 5), and the user can freely choose to use other downloaded applications 196 without medical device restrictions. Note that the mobile device graphical user interface 197 can provide the MDA icon, thus allowing the user to later and securely configure the mobile device and communicate with his IPG as illustrated earlier (FIG. 4).

If medical device use is not indicated by the selection (308), MDA 300' allows the operating system to provide the mobile device graphical user interface 197 (FIG. 5) to the patient (324), as described earlier with respect to FIG. 9A. Again, the mobile device graphical user interface 197 can provide the MDA icon, thus allowing the user to later and securely configure the mobile device and communicate with his IPG (FIG. 4), even if he did not select to so use the mobile device in this manner during the booting process.

As with MDA 300, MDA 300' can be provided to a patient in any number of ways. The MDA 300' may comprise an executable file, or patch, which when executed will make the necessary changes to the operating system to allow receipt of the user's selection during booting, and to automatically run at least some or all of the aspects of the MDA 200 when booting has completed. MDA 300' thus can also include these aspects, such as the MDA graphical user interface 198 (FIG. 8) (318) and possibly also aspects dealing with initialization (316). When the patch is executed, these aspects of MDA 200 may also be automatically installed and run as discussed above. Alternatively, these aspects of MDA 200 may be separately downloaded (e.g., as an "app") separate from the patch.

One skilled in the art will understand that the disclosed medical device applications will comprise instructions that can be stored on non-transistory machine-readable media, such as magnetic, optical, or solid-state discs, integrated circuits, tapes, etc., and which can be executed on the mobile device. Examples of likely storage devices having machine-readable media which would store the disclosed medical device applications include the mobile device 150 (e.g., after its downloaded, on its hard drive), or an Internet or other network server, such as an implantable medical device manufacturer's server or an app store server, which a user can access to download the medical device application to his mobile device as noted previously. However, other storage devices could include disks, memory sticks or modules, which may be portable or which may be integrated within other computers or computer systems.

Although particular embodiments have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:
1. A system, comprising:
   an implantable medical device; and
   a storage device comprising a medical device application stored in a non-transitory machine-readable medium configured for execution by a mobile device, wherein the medical device application is configured to store state information for:
   (a) one or more hardware modules determined by the medical device application to interfere with operation as a medical device; and

(b) one or more software tasks active in the mobile device determined by the medical device application to interfere with operation as a medical device;

initialize the mobile device from a first configuration into a second configuration for use as a medical device by:

(c) disabling or reconfiguring one or more hardware modules; and (d) suspending or terminating one or more software tasks; and provide a graphical user interface to the initialized mobile device to enable the mobile device to communicate with an implantable medical device during a communication session, wherein the graphical user interface allows for exciting of the medical device application, whereby the medical device application will retrieve the state information and use the state information to:

(e) enable the one or more hardware modules that were disabled in step (c) or to restore the one or more hardware modules that were reconfigured in step (c) before the medical device application stops; and (f) resume the one or more software task that were suspended in step (d) before the medical device application stops.

2. The system of claim 1, wherein step (a) comprises:
identifying hardware modules in the mobile device; and
comparing the identified hardware modules to a list of hardware modules provided by the medical device application to determine which of the one or more hardware modules to disable or reconfigure.

3. The system of claim 1, wherein step (b) comprises:
identifying active software tasks in the mobile device; and
comparing the identified software tasks to one or more lists of software tasks to determine which of the one or more software tasks to suspend or terminate.

4. The system of claim 1, wherein the graphical user interface allows a user to set or adjust therapy settings of the implantable medical device.

5. The system of claim 1, wherein the graphical user interface allows a user to receive data from the implantable medical device.

6. The system of claim 1, wherein the graphical user interface allows a user to review contraindication information concerning the implantable medical device.

7. The system of claim 1, wherein one or both of steps (c) and (d) are also periodically performed during the communication session.

8. The system of claim 1, wherein the storage device comprises the mobile device.

9. The system of claim 1, wherein the storage device comprises an Internet server or other network server accessible by the mobile device.

10. The system of claim 1, wherein the medical device application is selectable for execution as an icon on a display of the mobile device.

* * * * *